United States Patent [19]
DeSena

[11] Patent Number: 5,193,106
[45] Date of Patent: Mar. 9, 1993

[54] X-RAY IDENTIFICATION MARKER

[76] Inventor: Danforth DeSena, 4 Ivie Rd., Cape Elizabeth, Me. 04107

[21] Appl. No.: 573,897

[22] Filed: Aug. 28, 1990

[51] Int. Cl.$^5$ .............................................. H05G 1/28
[52] U.S. Cl. ................................... 378/163; 378/204; 378/205
[58] Field of Search ................ 378/162, 163, 164, 205, 378/204

[56] References Cited

U.S. PATENT DOCUMENTS

| | | | |
|---|---|---|---|
| 3,836,776 | 9/1974 | Gullekson | 378/162 |
| 4,506,676 | 3/1985 | Duska | 378/162 |
| 4,813,062 | 3/1989 | Gilpatrick | 378/162 |
| 4,860,331 | 8/1989 | Williams et al. | 378/163 |
| 4,985,019 | 6/1991 | Michelson | 378/164 |

*Primary Examiner*—Constantine Hannaher
*Assistant Examiner*—Don Wong
*Attorney, Agent, or Firm*—Thomas L. Bohan

[57] ABSTRACT

A device for marking cutaneous landmarks as a means of identifying under x-radiography pathological deep structures of the small bones of the foot that comprises affixing a radiopaque material to an adhesive tape and placing the radiopaque material over a cutaneous landmark on a patient's foot and then x-raying the highlighted area. The radiopaque material is formed into any one of a variety of shapes, such as a circle, triangle or square, so as to provide a marker that completely encompasses the cutaneous landmark. A series of such markers is affixed to a roll of tape with an adhesive backing, or provided in pre-cut form, for ease of dispensation and attachment to the patient's foot.

10 Claims, 4 Drawing Sheets

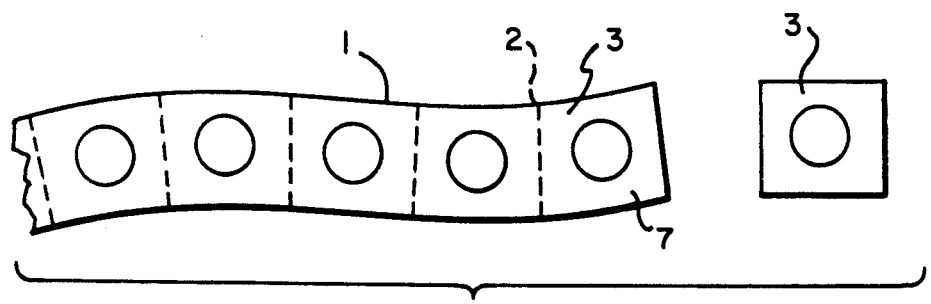
FIG. 1A
FIG. 1B
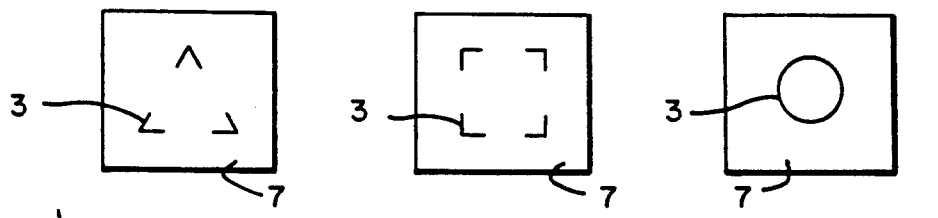
FIG. 2
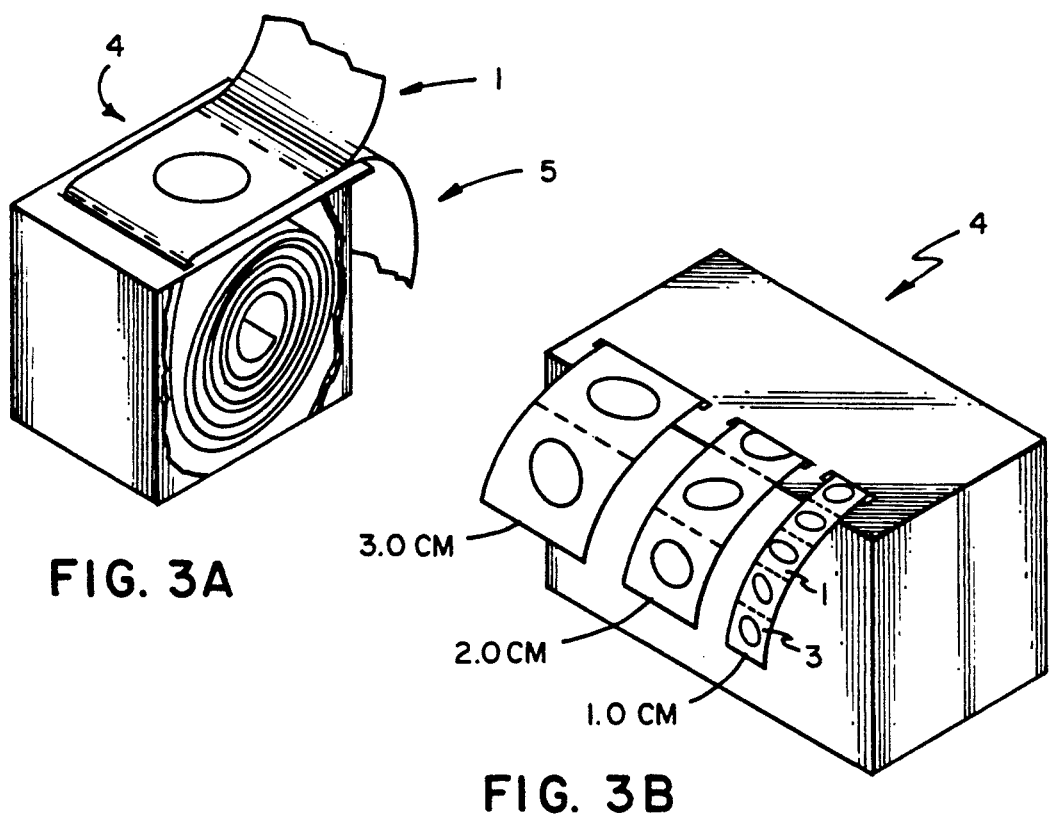
FIG. 3A
FIG. 3B

X-RAY IDENTIFICATION MARKER

BACKGROUND OF THE INVENTION

1. Field of the Invention

The invention relates to the field of devices for providing cutaneous-based markings in association with x-ray examination procedures. More particularly, the invention relates to a marker device to be used in podiatric evaluations, wherein the marker device encompasses and defines the area under visual examination in such a way that this area can later be correlated with a radio-photograph.

2. Description of the Prior Art

In the field of podiatric evaluations there is often times great difficulty in determining the type and location of a sub-cutaneous problem (under the skin). In particular, while naturally-occurring cutaneous landmarks, such as palpable masses and cutaneous lesions, indicate that there may be a deep structure problem in a foot, it is generally impossible to determine—in the absence of x-ray photographs—whether the problem is associated with a bone of the foot, and if it is, which bone is the source of the problem. Highlighting the area of interest with a marker that is easily seen on the radiograph focuses the podiatrist's attention and thus aids in determining the course of treatment. Failure to so mark the radiograph, or marking in such a way that even small portions of the area of interest are obscured may seriously hinder the diagnostic examination of the problem area. Inadequate diagnostic examination can then lead to improper and/or inadequate treatment.

Present methods of converting visual localization to x-ray localization vary, but generally all involve the use of a radiopaque material—such as barium sulfate or lead—to highlight the area of interest. Commonly, the radiopaque material is placed on (or in) the patient prior to the radiography; however, one technique involves placing the radiopaque material directly on the photographic medium which is to be exposed to the x-radiation. This technique relies on the coordination among the examining physician, the x-ray technician, and the radiologist. In many cases this coordination is not possible; in others the information provided is too general and the probability of improperly marking and evaluating the area of interest is heightened.

Another technique, described by Duska (U.S. Pat. No. 4,506,676), utilizes an adhesive tape with the radiopaque material incorporated into the tape, which tape is then applied to the patient's skin. As it is added to the tape, the radiopaque material is formed into a plurality of arrows or dots. The tape is then placed on the patient's body so that the image of the radiopaque symbols point to the area of interest on the x-ray film. A major shortcoming of the Duska technique is that it tape only extends up to, and does not surround, the area of interest. Its usefulness is thus limited to the evaluation of large bones, such as the bones of the legs and arms; in the examination of small bones, such as those of the feet, the Duska marker does not adequately focus attention on the critical area. This is primarily due to the size of the Duska marker; it is simply too large to place close to the cutaneous landmark without obscuring the subcutaneous problem. Finally, for fine work, such as in the examination of the small bones of the toes, it is useful to completely delineate the cutaneous area in question, preferably by encircling it rather than pointing at it.

A marker disclosed by Williams et al. (U.S. Pat. No. 4,860,331) comprises a tape with a plurality of index markings, wherein the tape is affixed to the patient's skin. The tape is a flexible one which cannot be accidently shifted or dislodged. The Williams marker provides an indexing means of identification for regions of the body which are subjected to scanning procedures such as computerized axial tomography. Rather than encompass small areas of interest, the Williams marker provides reference lines only. These lines may obscure rather than encompass an area of interest as small as individual bones of the toes. The Williams marker may be effective in indexing cross-sectional scans of the entire body, but it would hinder podiatric evaluations of much smaller areas of interest.

A further technique utilized to mark an area of interest is the three-dimensional marker disclosed by Gulleckson (U.S. Pat. No. 3,836,776). The three-dimensional marker has three elongated members disposed at right angles to each other and is normally embedded in a patient's wound in order to ensure proper positioning. The problem with this technique, in addition to its being painful, is that it is limited to pinpointing foreign objects in the body (somewhere in the vicinity of the wound) and therefore is generally not applicable to the examination of bones of the foot; among other disadvantages, the three-dimensional marker may actually obscure the area of interest.

A still further technique highlights the distinction between the needs of the various medical specialties when it comes to markers on x-ray films. An example of particular relevance to the present application is podiatry. Podiatrists are involved primarily in the evaluation of the small bones of the feet and are frequently concerned with isolating for examination very small subcutaneous areas based upon cutaneous landmarks which often exist on irregular surfaces in hard-to-reach locations. To overcome these particular problems, podiatrists commonly use a marking technique that involves forming a piece of wire into a loop, taping the loop around the area of interest and then taking the x-ray. One of the many drawbacks of this technique is that it takes the podiatrist a considerable amount of time to prepare the marker. Another problem is that the loops formed are often of nonuniform shape and size. The podiatrist may end up with a marker that encompasses the area of interest and is suitable for use with the small bones of the feet, but one which nevertheless results in considerable inconvenience to the podiatrist and which furthermore imposes on the podiatrist's time with his or her patient. An x-ray technique involving the use of a set of readily dispensable markers of various sizes and shapes which can encompass the area of interest would therefore increase the diagnostic efficiency and effectiveness of the podiatrist.

It is therefore an object of the present invention to overcome the problems associated with the prior art markers by providing to podiatrists a marker to be used in the evaluation of the small bones of the feet that will sharply delineate an area of interest without obscuring it.

It is another object of the present invention to provide to podiatrists markers of standard shapes and sizes which are readily accessible, easily dispensable, and which require no manipulation by the podiatrist at the point of deployment.

SUMMARY OF THE INVENTION

The present invention overcomes the problems of the prior art by mounting onto tape radiopaque material in shapes designed to enclose small cutaneous landmarks in such a manner that the radiopaque shapes can be easily deployed on the patient's foot. Shapes such as circles, triangles and squares have been found to work satisfactorily. Typically, the circular shape is provided in sizes ranging from about 1.0 up to about 3.0 centimeters in inner diameter. The radiopaque material may be in powder, wire, or paint form; metallic materials such as barium sulfate, aluminum, and lead, may be used. A marker is thereby formed which is thin and flexible enough that it will conform to the irregular surface to be evaluated. A thin and flexible marker will also reduce patient discomfort when that patient is required to stand on the marker for a particular view of the area of interest.

In the present invention the radiopaque material, in any one of the shapes described, is affixed to a tape which has adhesive backing. Individual markers are pre-cut from a length of tape and packaged for easy removal and deployment. Another means of easily deploying individual markers involves the addition of perforations to the length of tape, wherein the perforations alternate with the individual markers. The perforated tape is then packaged in individual or multi-pack dispensers for convenient utilization in the radiology laboratory. To further assist the podiatrist, adhesive tapes of various colors, corresponding to different radiopaque shapes and internal dimensions, may be deployed from a multi-pack of boxes or rolled-tape dispensers.

To use the marker, a podiatrist removes it from a box or dispensing roll and attaches it to the patient's foot directly over a cutaneous landmark, such as a palpable mass or other lesion. An x-ray photograph is then taken of the area of interest. The radiopaque marker, by enclosing the area, focuses the attention of the podiatrist reviewing the x-ray photograph on the highlighted subcutaneous problem. This small-scale isolation assists in the determination of the size, location and extent of bone growths and other pathologies. Several examples where such isolation is of critical importance when examining the foot include: (1) when the patient has a joint irregularity and the cutaneous landmark consists of a symptomatic heloma (corn) between two toes; (2) when the patient has an exostosis and the landmark is again a heloma; (3) when the patient has a plantar prominent metatarsal and the particular metatarsal must be identified; (4) when the patient has a palpable mass and there is no bone structure problem, such as in differentiating between a verruca (wart) and a plantar tyloma (callus); and (5) when the patient has a foreign body embedded in the foot.

The present invention specifically addresses the problems listed above which now confront podiatrists in their examinations of patients with cutaneous landmarks. Currently-available marking systems are too cumbersome for podiatrists, particularly when the pathology is between the toes, where the greatest frequency of bone-related cutaneous lesions occur. The novelty and utility of the present invention resides in its ability to mark areas of interest with markers that are large enough to *encompass* the region of interest, but small enough not to obscure the subcutaneous problem and, also, thin and flexible enough to be readily applied to the irregular surfaces commonly of interest to podiatrists. It thus addresses a long-felt need in the field of podiatry.

BRIEF DESCRIPTION OF THE DRAWINGS

FIG. 1a is a top view of a roll of markers, with perforations between each marker.

FIG. 1b is a side view of a marker detached from its non-stick backing.

FIG. 2 is a top view of three marker configurations.

FIG. 3a is a side view of a single marker tape dispenser. FIG. 3b is a front view of a pack of a set of various sized markers.

FIG. 7b is an axial view of the foot of FIG. 7a.

FIG. 8b is the lateral view of the foot of FIG. 8a.

FIG. 9b is the lateral view of the foot of FIG. 9a.

PREFERRED EMBODIMENT OF THE INVENTION

Figure 4:
FIG. 4 is a side view of a foot with a cutaneous landmark enclosed by a marker.

FIG. 1a is a top view of a series of marker devices 3 of the present invention. Said marker devices 3 comprise a pressure sensitive adhesive medical tape 1 onto which a flexible radiopaque material is affixed. Said tape 1 may be any of a number of pressure sensitive tapes, well known in the field, that is, preferably, hypo-allergenic. Said tape 1 comprises one non-adhering surface and one surface containing a pressure sensitive adhesive. Further, a roll of said tape 1 contains a plurality of perforations 2 separating individual segments 7. Each of said individual segments 7 contains one encompassing shape formed of said radiopaque material, wherein said radiopaque material is applied to said non-adhering surface of said individual segments 7 by either painting or vapor deposition means. A non-stick backing 5 is affixed to said pressure sensitive adhesive side of said tape 1. Said roll of said tape 1 containing said individual segments 7 is then placed into a dispenser 4 for ease of dispensation, as illustrated in FIG. 3a. As illustrated in FIG. 3b, a plurality of dispensers is arrayed to offer a podiatrist a variety of marking shapes and sizes.

In the preferred embodiment of the present invention the radiopaque material aluminum is affixed to said adhesive tape 1 by vapor deposition. Specifically, a stencil of a plurality of circles, each about 2.0 centimeter inner diameter, is placed on said non-adhering surface of said tape 1. It is to be noted that said stencil may consist of a variety of markers with different shapes and sizes. Each of said plurality of shapes alternates with each of said plurality of perforations 2. Said aluminum is then vapor deposited through said stencil and onto said adhesive tape 1. In the preferred embodiment said aluminum is deposited on to said adhesive tape 1 to a thickness sufficient to highlight an area of interest with clarity. Said stencil is then removed and then said tape 1, with said aluminum and said non-stick backing 5 affixed thereto, is formed into a roll for ease of dispensation from said dispenser 4.

The method by which the present invention is used, is illustrated generally in FIG. 4. To isolate a particular area of concern for examination, said marker 3 is affixed to a patient's skin directly over a palpable mass (such as a palpable arthritic spur or a palpable foreign body), or over a cutaneous lesion (such as a plantar ulceration or a digital hematoma). By positioning said marker 3 over one of these cutaneous landmarks, said radiopaque material, which encloses the area of concern, is superimposed upon and highlights the area associated with a problematic deep structure when x-ray photographs are taken.

Figure 5:
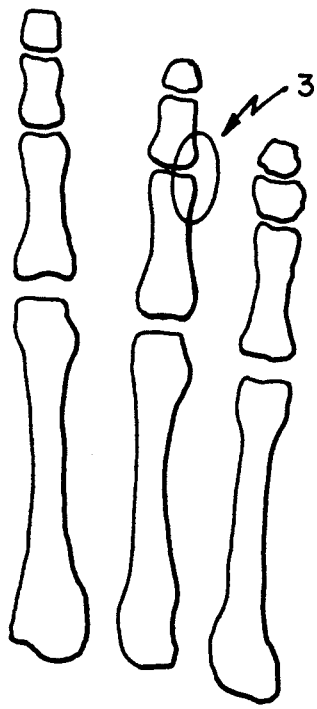
FIG. 5 is a dorsal-plantar (top) view of a foot with a joint irregularity.
Figure 6:
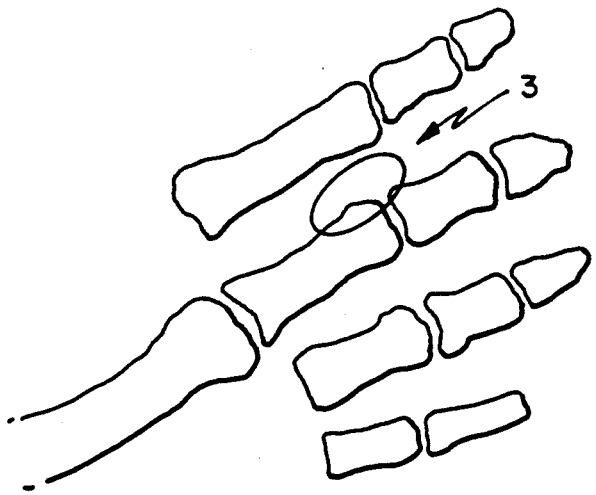
FIG. 6 is an oblique view of a foot with an exostosis.
Figure 7A:
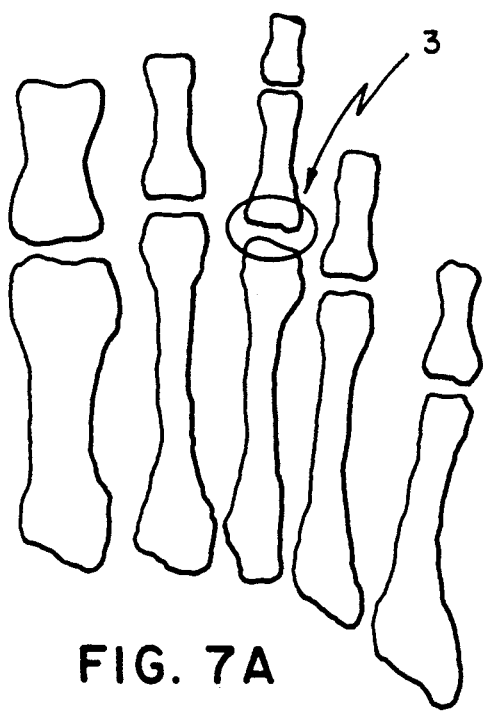
FIG. 7a is a dorsal-plantar view of a foot with a plantar prominent metatarsal.
Figure 7B:
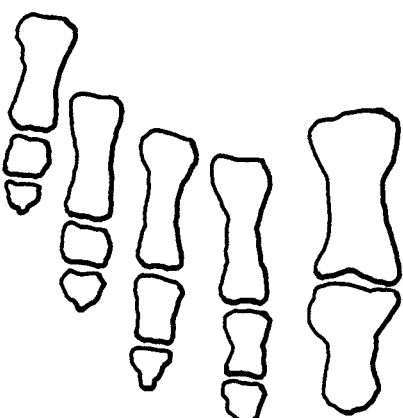
Figure 8A:
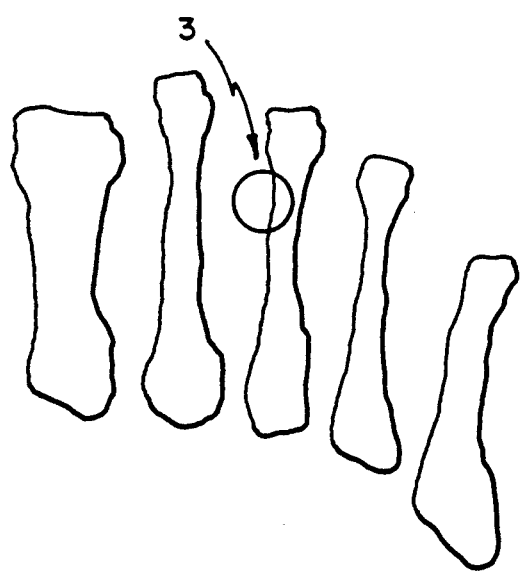
FIG. 8a is a dorsal-plantar view of a foot with wart.
Figure 8B:
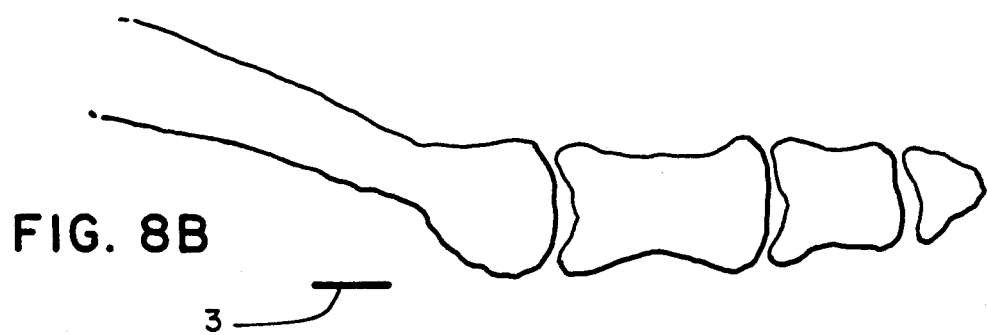
Figure 9A:
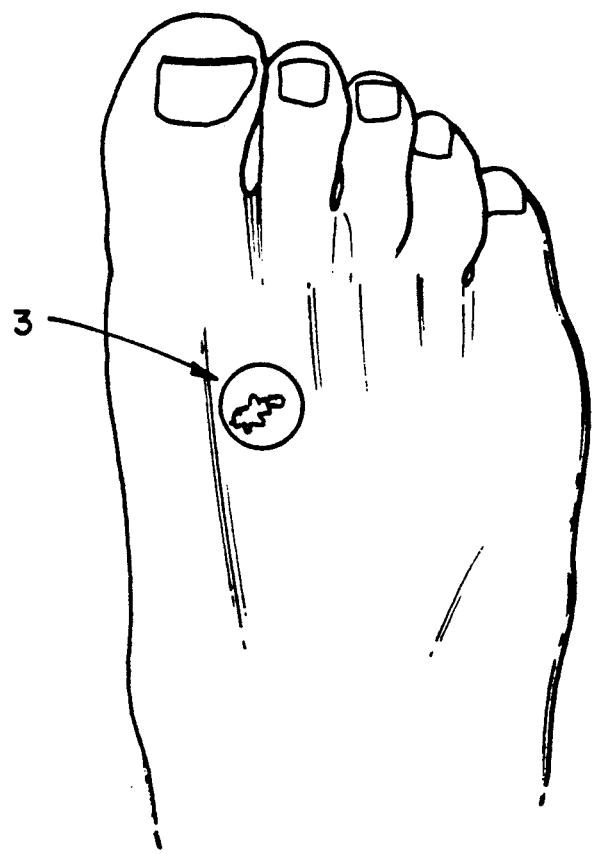
FIG. 9a is a dorsal-plantar view of a foot with an embedded foreign object.
Figure 9B:
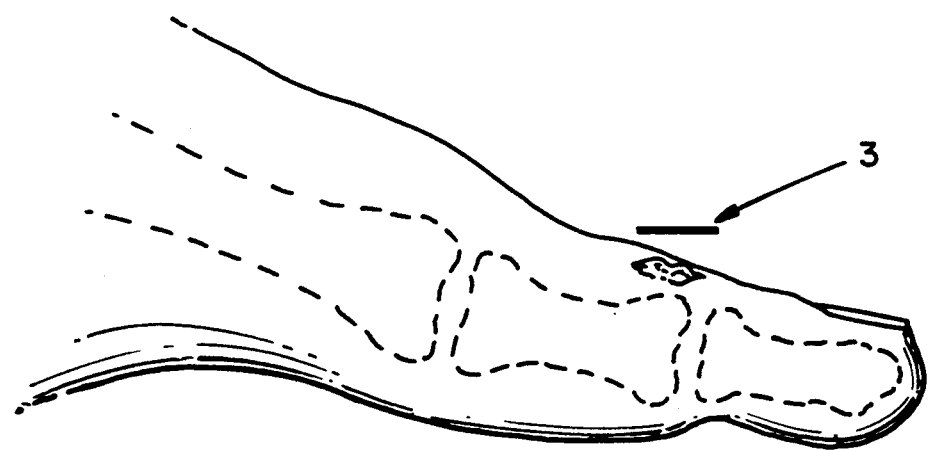

FIGS. 5 to 9b illustrate typical problem areas to which the present invention is addressed. In FIG. 5 said marker 3 is placed on a symptomatic heloma between two toes. An x-ray confirms that said heloma is associated with an excessively prominent lateral interphalangeal joint margin. In FIG. 6 said marker is again placed on a symptomatic heloma between two toes, only this time said heloma is associated with an exostosis on a medial-distal aspect of the third proximal phalanx. In FIGS. 7a and 7b said marker 3 indicates that a patient's plantar ulcer is due to a metatarsal extending too far down below the horizontal plane of neighboring metatarsals. In FIGS. 8a and 8b said marker 3 placed on a cutaneous landmark assists in differentiating between a verruca (wart) and a plantar tyloma (callus). The former is not caused by a prominent bone, while the later is; thus, different treatment is required. In FIGS. 9a and 9b said marker 3 is placed over a palpable mass on the dorsum of the foot to highlight that the subcutaneous problem is a foreign object embedded between the first and second metatarsals. Each situation illustrates that in the field of podiatry a variety of subcutaneous problems may all have the same cutaneous landmark. For this reason, it is necessary to provide a marker that focuses the podiatrist's attention directly on the area of interest without obscuring the problem.

Although the preferred embodiment of the invention has been described, it is to be remembered that the above description is merely illustrative. Other methods may be employed to form the marker of the invention, including, but not limited to, the use of a radiopaque spray-on paint or pre-forming of radiopaque wires into the shapes of interest. In addition, radiopaque materials other than aluminum may be employed to provide sufficient clarity to the marker encompassing the area of interest. Accordingly, it is to be understood that the present invention is not limited to that precisely shown and described herein.

I claim:

1. A marker device to be used in the x-ray examination of problematic deep structures of the foot, wherein said problematic deep structures of the foot are denoted by cutaneous landmarks, said marker device comprising:
    a. a tape with pressure-sensitive adhesive on one surface thereof and a non-adhering surface on a side opposite, wherein said tape is suitable for attachment to the surface of the skin of the foot, and
    b. a radiopaque material affixed to said non-adhering surface of said tape, wherein said radiopaque material is formed into a shape such that it completely surrounds a cutaneous landmark in a surrounding shape of an internal size comparable to that of cutaneous landmarks of podiatric pathologies.

2. A marker device as claimed in claim 1 wherein said radiopaque material is formed into the shape of a circle.

3. A marker device as claimed 2 wherein said circle has an inner diameter between about 1.0 centimeter and about 3.0 centimeters.

4. A marker device as claimed in claim 1 wherein said radiopaque material is affixed to said non-adhering surface of said tape by means of vapor deposition.

5. A marker device as claimed in claim 4 wherein said radiopaque material is aluminum.

6. A marker device to be used in the x-ray examination of problematic deep structures of the foot, wherein said problematic deep structures of the foot are denoted by cutaneous landmarks, said marker device comprising:
    a. a tape with pressure-sensitive adhesive on one surface thereof and a non-adhering surface on a side opposite, wherein said tape is suitable for attachment to the surface of the skin of the foot,
    b. radiopaque material, wherein said radiopaque material is deposited onto said non-adhering surface of said tape to form a plurality of circles, wherein each of said circles has an inner diameter of a dimension sufficient to completely surround cutaneous landmarks of podiatric pathologies, and
    c. a plurality of sets of perforations incorporated into said tape, wherein each of said plurality of circles is affixed to said tape between each pair of adjacent sets of perforations.

7. A marker device as claimed in claim 6 wherein each of said plurality of circles has an inner diameter between 1.0 centimeter and 3.0 centimeters.

8. A marker device as claimed in claim 6 wherein said radiopaque material is aluminum.

9. A marker device as claimed in claim 6 wherein said radiopaque material is affixed to said non-adhering surface of said tape by vapor deposition means.

10. A marker device as claimed in claim 6 further comprising tape dispensing means.

* * * * *